United States Patent [19]

Kumazawa et al.

[11] Patent Number: 4,937,200

[45] Date of Patent: Jun. 26, 1990

[54] METHOD OF EFFECTING IMMUNOASSAY BY USING AFFINITY CHROMATOGRAPHY

[75] Inventors: Toshiaki Kumazawa; Makoto Nakamura, both of Hachioji; Eriko Kogure, Sagamihara, all of Japan

[73] Assignee: Olympus Optical Co., Ltd., Japan

[21] Appl. No.: 32,501

[22] Filed: Mar. 31, 1987

[30] Foreign Application Priority Data

Apr. 9, 1986 [JP] Japan .................................. 61-79992

[51] Int. Cl.$^5$ .......................................... G01N 33/543
[52] U.S. Cl. .................................. 436/518; 436/161; 436/541; 364/497
[58] Field of Search ................. 436/541, 518, 161; 530/413; 210/198.2, 635; 422/70, 89; 73/23.1, 61.1 C

[56] References Cited

U.S. PATENT DOCUMENTS

| | | | |
|---|---|---|---|
| 3,475,600 | 10/1969 | Spence | 364/497 X |
| 3,506,818 | 4/1970 | Smith | 364/497 X |
| 3,555,260 | 1/1971 | Karohl | 364/497 |
| 3,562,501 | 2/1971 | Mears | 364/497 |
| 3,614,408 | 10/1971 | Watkin et al. | 364/497 X |
| 3,797,300 | 3/1974 | Sato | 364/497 X |
| 4,039,652 | 8/1977 | Adams | 436/541 X |
| 4,145,406 | 3/1979 | Schick | 436/541 |
| 4,357,668 | 11/1982 | Schwartz et al. | 364/497 |
| 4,385,991 | 5/1983 | Rosevear | 210/635 |
| 4,431,544 | 2/1984 | Atkinson | 210/502.1 X |
| 4,802,102 | 1/1989 | Lacey | 364/497 |

OTHER PUBLICATIONS de Alwis, Anal. Chem. vol. 57, 1985, pp. 2754–2756.
H. Oster, Prozess Chematographie, Frankfort 1973, p. 263.

*Primary Examiner*—Robert J. Hill, Jr.
*Attorney, Agent, or Firm*—Arnold, White & Durkee

[57] ABSTRACT

A method of effecting an immunoassay using affinity chromatography which a sample is injected into a reusable column charged with antibody applied on a solid support, an eluent is injected into the column to elute antigen bound with the antibody on the solid support, and an amount of eluted antigen is measured. In order to mitigate the influence of carry-overs of successive samples, blank values are corrected such that they include the carry-overs of previously measured samples, while elution time periods are kept constant. In one embodiment, the elution time periods are corrected such that blank values for respective samples are made constant.

3 Claims, 2 Drawing Sheets

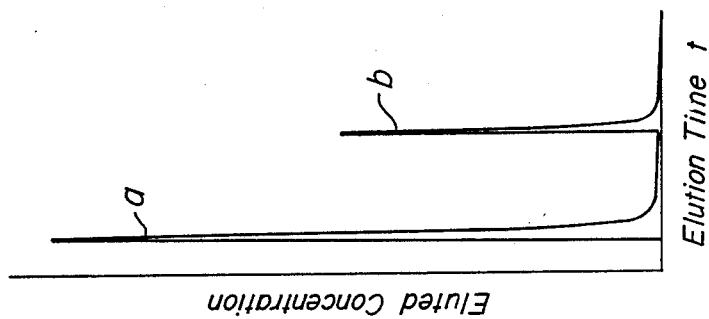
FIG_2
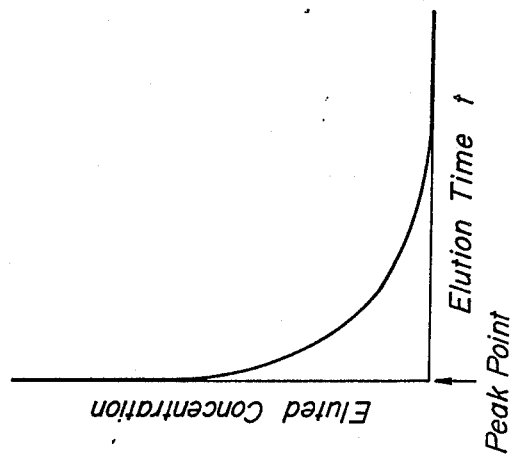
FIG_1

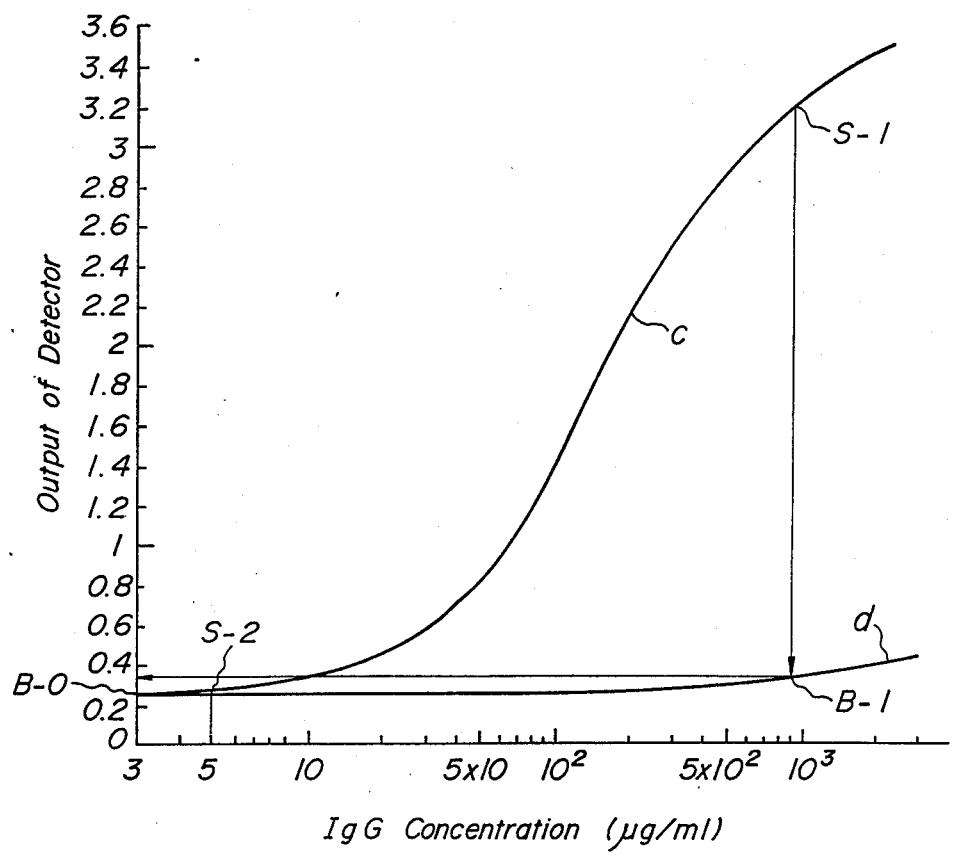
FIG_3

METHOD OF EFFECTING IMMUNOASSAY BY USING AFFINITY CHROMATOGRAPHY

BACKGROUND OF THE INVENTION

Field of the Invention and Related Art Statement

The present invention relates to a method of effecting an immunoassay by using affinity chromatography.

The immunoassay using the antigen-antibody reaction may be roughly classified into a labeling immunoassay using labeling substances and a non-labeling immunoassay in which the antigen-antibody complex or conjugate is directly measured without using the labeling substances. These immunoassays may be further classified into various methods. For instance, the labeling immunoassay may be classified into radio immunoassay, enzyme immunoassay, fluorescence immunoassay and others. Further, in accordance with the manner of reaction, the immunoassay may be classified into a competitive method and a non-competitive (sandwich) method. Moreover, the immunoassay may be further classified into a heterogeneous method and a homogeneous method. In the heterogeneous method, a so-called B-F separation is required for separating an immuno complex (Bound) which is produced as the result of the antigen-antibody reaction and non-reacted antigen or antibody (Free).

Among the above mentioned various methods, the heterogeneous method has recently become predominant. As one of the heterogeneous methods, there has been developed an immunoassay using affinity chromatography in which successive samples are injected into a reusable column packed with ligands such as antibody or antigen attached to a solid support to effect the antigen-antibody reaction in the column, and after the reaction, the bound antigen or antibody is measured with the aid of labeling substances and then the bound antigen or antibody is eluted or dissociated with the aid of an eluent.

The above mentioned immunoassay using the affinity chromatography has been disclosed in greater detail in "ANALYTICAL CHEMISTRY", Vol. 57, No. 14, DECEMBER 1985, pp 2754 to 2756. In this known method, in order to measure mouse anti-bovine IgG contained in a sample, Reactigel-6X (Pierce Chemical Co., Rockford) having bovine IgG applied thereto is charged in a microreactor. Then, the sample (mouse anti-bovine IgG), a labeling antibody (anti-mouse IgG-glucose oxidase) and a substrate (glucose) are successively injected into the microreactor, and an amount of produced hydrogen peroxide is measured by means of an electric chemical measuring device such as a thin-layer amperometric detector to derive an amount of the mouse anti-bovine IgG contained in the sample. After the measurement for a sample is done, a disruption buffer of pH 2.0 is injected into the column to elute the bound complexes. Next, an assay buffer of pH 6.8 of a next sample is injected into the microreactor.

In the known immunoassay method explained above, various timings during the measurement are fixedly determined as illustrated in FIG. 4 of said article. If bound complexes or conjugates could not be sufficiently eluted, there might be produced undesired carry-over of sample, and measurement error might be introduced. Therefore, eluting and reproducing time periods have to be made long. However, if a sample has an extremely high concentration, the carry-over could not be removed sufficiently. Moreover, if a sample concentration is low, the eluting and regenerating time periods would be considered unnecessarily long, and the efficiency of the process would become low.

As explained above, in the immunoassay using affinity chromatography, undesired carry-over might be introduced among samples unless the bound antigen or antibody is sufficiently eluted. The carry-over would be remarkable after the measurement of samples having high concentrations. That is to say, after a high concentration sample is measured, when a low concentration sample is analyzed, a blank value might be erroneously judged as a measured value. The above mentioned problem could be avoided or mitigated by prolonging the eluting period sufficiently. However, an elution rate (an amount of eluted substance per unit time) becomes slow in accordance with the progress of the elution, and thus in order to effect a sufficient elution, the elution time period has to be set very long, so that the efficiency of process might be decreased.

SUMMARY OF THE INVENTION

The present invention has for its object to provide a method of effecting an immunoassay by affinity chromatography, in which method samples can be measured very accurately without being affected by the carry-over, and at the same time a number of samples can be measured efficiently.

According to the invention, in a method of measuring given substances contained in samples in an immunological manner by injecting samples through a reusable column charged with ligands attached to a solid support to effect an antigen-antibody reaction, injecting an eluent through the column to elute bound substances out of the column, and measuring eluted substances, the improvement comprises a step of correcting measured values in accordance with elution characteristics of previously measured one or more samples under the existence of the eluent.

DESCRIPTION OF THE PREFERRED EMBODIMENTS

FIG. 1 shows a chromatograph of the immunoassay using the affinity chromatography;

FIG. 2 is a graph illustrating an elution characteristic; and

FIG. 3 is a graph explaining the carry-over between successive samples.

DESCRIPTION OF THE PREFERRED EMBODIMENTS

Now several embodiments of the method of effecting the immunoassay using affinity chromatography according to the invention will be explained.

First Embodiment

Carriers to be charged in a column of affinity chromatography were prepared in the following manner.

First 0.3 g of amino alkalized glass carriers having a mesh of 125 to 200 and a pore size of 2,000 Å and 5 ml of 5% glutaraldehyde water solution were reacted with each other at 25° C. for one hour to effect the aldehydization.

Then the carriers were washed with water and were put in a solution containing 5 mg of anti-human IgG monoclonal antibody and a reaction was carried out at 4° C. for eight hours to fix the anti-human IgG monoclonal antibody on the carriers.

Then, 2 ml of 0.1 M phosphate buffered saline (PBS) pH 7.5 of 10% water soluble gelatin was added and the whole solution was incubated at 4° C. for twelve hours to block non-specific protein binding sites.

Next, the carriers were sufficiently washed with 0.1 M PBS pH 7.5, and then 2 ml of 1 M PBS pH 7.5 and 5 mg of NaBH$_4$ were added and the whole solution was incubated at 4° C. for five hours. Next, the carriers were washed with 0.01 M Tris-HCl buffer pH 7.8 containing 0.15 M NaCl. In this manner, there were obtained affinity chromatography carriers for human IgG.

The carriers were next charged in a column having an inner diameter of 2 mm and a length of 35 mm. Then use was made of as a washing liquid of 0.01 M Tris-HCl buffer pH 7.8 containing 0.15 M NaCl, an eluent liquid of 0.1 M glycine-HCl buffer pH2.5, and a sample of coarse globulin fractionated from human serum with 40% ammonium sulfate precipitation.

FIG. 1 shows a typical chromatograph. A curve a represents an elution characteristic of nonbound antigen in a sample and a curve b depicts an elution characteristic of antigen eluted out of the column during the eluting process. FIG. 2 shows the elution characteristic on an enlarged scale. As shown in FIG. 2, the elution rate of antigen is decreased greatly in accordance with the progress of the elution. Therefore, by making the elution time infinite, it is theoretically possible to elute all the antigens out of the column and the carry-over can be completely removed. However, in practice, it is impossible to make the elution time infinite, and a definite elution time has to be set. Therefore, the carry-over could not be removed practically.

FIG. 3 is a graph explaining the carry-over. In FIG. 3 the axis of abscissae denotes a concentration of a sample IgG ($\mu$g/ml) and the axis of ordinates represents an output value of a detector. A curve c denotes a sample value and a curve d denotes a blank value after the measurement of the antigen concentration of a sample. As can be understood from FIG. 3, a blank value B-1 (output value of 0.35) of a sample S-1 having a high IgG concentration ($9 \times 10^2$ $\mu$g/ml) becomes higher than a blank value B-0 (output of 0.25) prior to the measurement. Therefore, if a next sample S-2 having a low IgG concentration (5 $\mu$g/ml) is measured, there would be obtained a measured value of 0.37 which is higher than the actual value.

In order to solve the above drawback, in the present embodiment blank values are corrected in accordance with elution characteristics of previously measured samples, while the elution time period is kept constant.

The antigen-antibody reaction in the column may be expressed by the following equation:

$$\frac{[Ag] \cdot [Ab]}{[AgAb]} = K \tag{1}$$

wherein, Ag is antigen, Ab is antibody and K is an elution constant. Further, between an elution constant $K_1$ in the case of the antigen-antibody and an elution constant $K_2$ in the case of the elution under the existence of the eluent, the following relation is established.

$$K_1 << K_2 \tag{2}$$

Therefore, in the elution under the existence of the eluent, the following relationship is existent.

$$[Ag] \cdot [Ab] > [Ag\ Ab] \tag{3}$$

This means that in the column, the antigen and antibody are existent in the non-bound condition. Therefore, if the eluent is further passed through the column, the antigen is eluted out of the column. The elution characteristic is dependent upon a kind and an amount of the eluent, the construction of the column, temperature, elution time period, etc. These parameters may be easily made constant. Then, the elution characteristic may be expressed as shown in FIG. 2, while the elution time period is a sole variable parameter The elution characteristic may be expressed as follows.

$$P_B = \frac{P_{S1} \cdot A}{Y \cdot T} + P_0 \tag{4}$$

wherein
$P_B$: antigen concentration in an eluted solution after an elation time period T
$P_{S1}$: antigen concentration at a peak position (measured value)
A: constant (determined by temperature, shape of the column, etc.)
Y: elution constant (determined by a kind, a concentration and a flow rate of the eluent)
T: elution time period
$P_0$: blank value Therefore, an antigen concentration $P_{S2}$ of a second sample can be corrected with the aid of $P_B$ in the following manner.

$$\begin{aligned} P_{S2} &= P_S - P_B \\ &= P_S - \left( \frac{P_{S1} \cdot A}{Y \cdot T} + P_0 \right) \end{aligned} \tag{5}$$

wherein $P_S$ is a measured value of the antigen concentration (peak value) of the second sample. Similarly, an antigen concentration $P_{S3}$ a third sample can be corrected in the following manner.

$$P_{S3} = P_S - \left( \frac{P_{S1} \cdot A}{Y \cdot 2T} + \frac{P_{S2} \cdot A}{Y \cdot T} + P_0 \right) \tag{6}$$

In general, an antigen concentration $P_{(n)}$ of an $n^{th}$ sample can be derived from the following equation.

$$P_{(n)} = P_S - \sum_{k=1}^{n-1} \frac{A \cdot P_{S(k)}}{(n-k)T \cdot Y} - P_0 \tag{7}$$

In the present embodiment, measured values of successive samples are corrected in accordance with the elution characteristics of the previously measured samples so as to remove the influence of the carry-over. In this manner, the antigen concentrations of samples can be always measured very accurately.

Second Embodiment

In the present embodiment, elution time periods for respective samples are determined such that blank values including carry-overs of samples are made constant. That is to say, an elution time period t for a sample having an antigen concentration $P_S$ is determined, while the eluted antigen concentration $P_B$ becomes a given constant value. The constant concentration $P_B$ for respective samples can be expressed as follows.

First Measurement: $P_B = P_{S1} \cdot A/Y t_1 + P_0 \rightarrow t_1$ (8)

Second Measurement: $P_B = P_{S1} \cdot A/Y(t_1 + t_2) +$
$P_{S2} \cdot A/Y t_2 + P_0 \rightarrow t_2$ Third Measurement: $P_B = P_{S1} \cdot A/Y(t_1 + t_2 + t_3) +$
$P_{S2} \cdot A/Y(t_2 + t_3) + P_{S3} \cdot A/Y t_3 + P_0 \rightarrow t_3$ $n^{th}$ Measurement: $P_B = P_{S1} \cdot A/Y \cdot \sum_{k=1}^{n} t_k +$
$P_{S2} \cdot A/Y \cdot \sum_{k=2}^{n} t_k + P_{S3} \cdot A/Y \cdot$
$\sum_{k=3}^{n} t_k + \ldots + P_{Sn} \cdot A/Y \cdot t_n + P_0 \rightarrow t_n$ In the above equation (8), A, Y and $P_0$ are constants, so that a necessary elution time period $t_n$ for eluting the antigen out of the column to the given constant value $P_B$ can be derived from a measured value $P_{Sn}$ for a relevant sample, measured values $P_{S1}, P_{S2} \ldots P_{S(n-1)}$ and elution time periods $t_1, t_2 \ldots t_{n-1}$ for previous samples.

In this manner, by setting elution time periods for successive measurements such that the blank values $P_B$ inclusive of carry-overs are made constant, elution time periods for low concentration samples can be shortened and the influence of the carry-overs of high concentration samples can be decreased so that S/N of measured values can be improved.

Third Embodiment

In this embodiment elution time periods for successive samples are determined such that elution rates of dissociated antigen under the existence of the eluent are made constant. To this end, the above equation (8) is differentiated with respect to time, and necessary elution time periods for obtaining the constant elution rate are calculated.

In this manner, the carry-overs among a number of samples can be made substantially constant and thus the carry-over in respective measured values can be easily and accurately corrected.

The present invention is not limited to the above embodiments, but many modifications may be conceived by those skilled in the art. In the above embodiments, antigen contained in samples is measured by using the column charged with carriers having antibody fixed thereto. It should be noted various substances in samples other than antigen may be equally measured by using columns charged with carriers having various ligands applied thereto, said ligands being specifically reactive with substances to be analyzed.

What is claimed is:

1. A method of measuring given substances contained in samples in an immunological manner by injecting samples through a reusable column charged with ligands attached to a solid support to effect an antigen-antibody reaction, comprising the steps of:
   injecting an eluent through the column to elute bound substances out of the column;
   measuring eluted substances; and
   determining elution time periods for successive samples in accordance with the elution characteristics of the previously measured one or more samples such that a flow rate of an eluted substance is made equal to a predetermined constant value.

2. A method of measuring given substances contained in samples in an immunological manner by injecting samples through a reusable column charged with ligands attached to a solid support to effect an antigen-antibody reaction, comprising the steps of:
   injecting an eluent through the column to elute bound substances out of the column;
   measuring eluted substances; and
   correcting blank values of a sample measurement in accordance with elution characteristics of previously measured one or more samples;
   wherein said correcting step includes a step of deriving a corrected value $P_{(n)}$ of an $n^{th}$ sample in accordance with the following equation:

$$P_{(n)} = P_S - \sum_{k=1}^{n-1} \frac{A \cdot P_{S(k)}}{(n-k)T \cdot Y} - P_0$$

wherein $P_S$ is a non-corrected measured value of the relevant sample, $P_{S(K)}$ is a measured value of a $k^{th}$ sample, A is a constant determined by a temperature and a shape of the column, Y is an elution constant determined by kind, concentration and flow rate of the eluent, T is a constant elution time period, and $P_0$ is an initial blank value.

3. A method of measuring given substances contained in samples in an immunological manner by injecting samples through a reusable column charged with ligands attached to a solid support to effect an antigen-antibody reaction, comprising the steps of:
   injecting an eluent through the column to elute bound substances out of the column;
   measuring eluted substances; and
   correcting an elution time period in a measurement of a relevant sample in accordance with the elution characteristics of the previously measured one or more samples;
   wherein said correcting step includes a step of deriving a corrected elution time period $t_n$ for an $n^{th}$ sample in accordance with the following equation:

$$P_B = P_{S1} \cdot A/Y \cdot \sum_{k=1}^{n} t_k + P_{S2} \cdot A/Y \cdot \sum_{k=2}^{n} t_k + P_{S3} \cdot A/Y \cdot \sum_{k=3}^{n} t_k + \ldots + P_{Sn} \cdot A/Y \cdot t_n + P_0$$

wherein $P_S$ is the predetermined constant value, $P_{S1}, P_{S2} \ldots P_{Sn}$ are measured values of first, second . . . $n^{th}$ samples, A is a constant determined by a temperature and a construction of the column, Y is an elution constant determined by kind, concentration and flow rate of the eluent, and $t_1, t_2 \ldots t_{n-1}$ are elution time periods for first, second . . . $(n-1)^{th}$ samples, respectively.

* * * * *